United States Patent [19]

Gundelfinger

[11] 4,242,909
[45] Jan. 6, 1981

[54] SAMPLE INJECTOR

[75] Inventor: Richard Gundelfinger, Oakland, Calif.

[73] Assignee: Rheodyne Incorporated, Cotati, Calif.

[21] Appl. No.: 31,473

[22] Filed: Apr. 19, 1979

[51] Int. Cl.³ .............................................. G01N 1/12
[52] U.S. Cl. .............................. 73/422 GC; 73/423 A
[58] Field of Search ...................... 73/422 GC, 423 A; 422/63, 64, 70, 100

[56] References Cited

U.S. PATENT DOCUMENTS

| | | | |
|---|---|---|---|
| 3,530,721 | 9/1970 | Hrdina | 73/422 GC |
| 3,733,909 | 5/1973 | Golovistikov | 73/422 GC |
| 3,916,692 | 11/1975 | Abraham et al. | 73/422 GC |
| 3,918,913 | 11/1975 | Stevenson et al. | 73/422 GC |
| 3,961,534 | 6/1976 | Gundlefinger | 73/422 GC |
| 4,022,065 | 5/1977 | Ramin et al. | 73/422 GC |
| 4,094,196 | 6/1978 | Friswell | 73/422 GC |
| 4,182,184 | 1/1980 | Bakalyar | 73/422 GC |

*Primary Examiner*—S. Clement Swisher
*Attorney, Agent, or Firm*—Freilich, Hornbaker, Wasserman, Rosen & Fernandez

[57] ABSTRACT

An apparatus is described for withdrawing liquid samples from vials and injecting them into a chromatographic column or other analyzing device, which minimizes wastage, cross contamination, and dilution of the samples, and which can be automated with a minimum of complexity. The apparatus includes a sample loop for receiving a sample, and then delivering the sample by means of an injector valve into the flow stream of a chromatographic column, wherein an outer end of the loop is detachably connected to the valve by a loop end seal. The outer loop end can be lifted from the loop end seal and dipped into a vial, and a syringe connected via the valve to the inner loop end can be operated to draw sample liquid into the loop. The outer loop end then can be lifted from the vial and reinserted into the loop end seal, and upon operation of the valve the outer loop end is connected into the flow stream that is injected into the column to carry the sample to the column.

8 Claims, 9 Drawing Figures

LOAD

INJECT

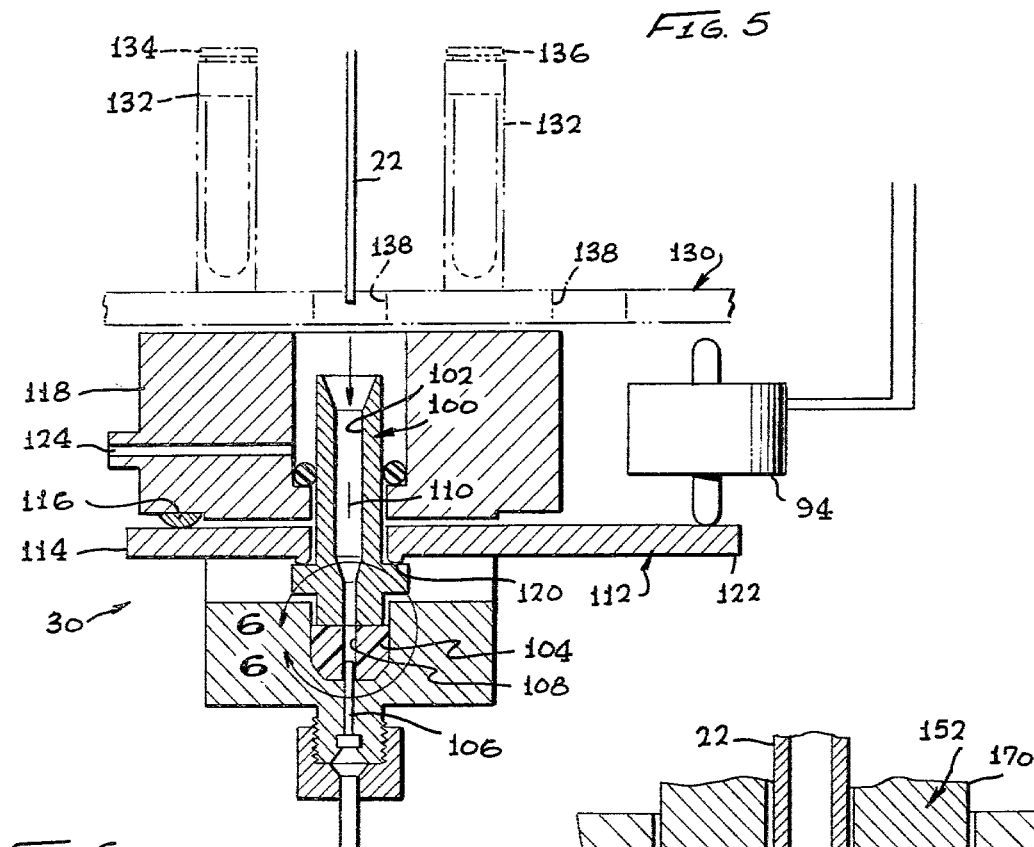
FIG. 5
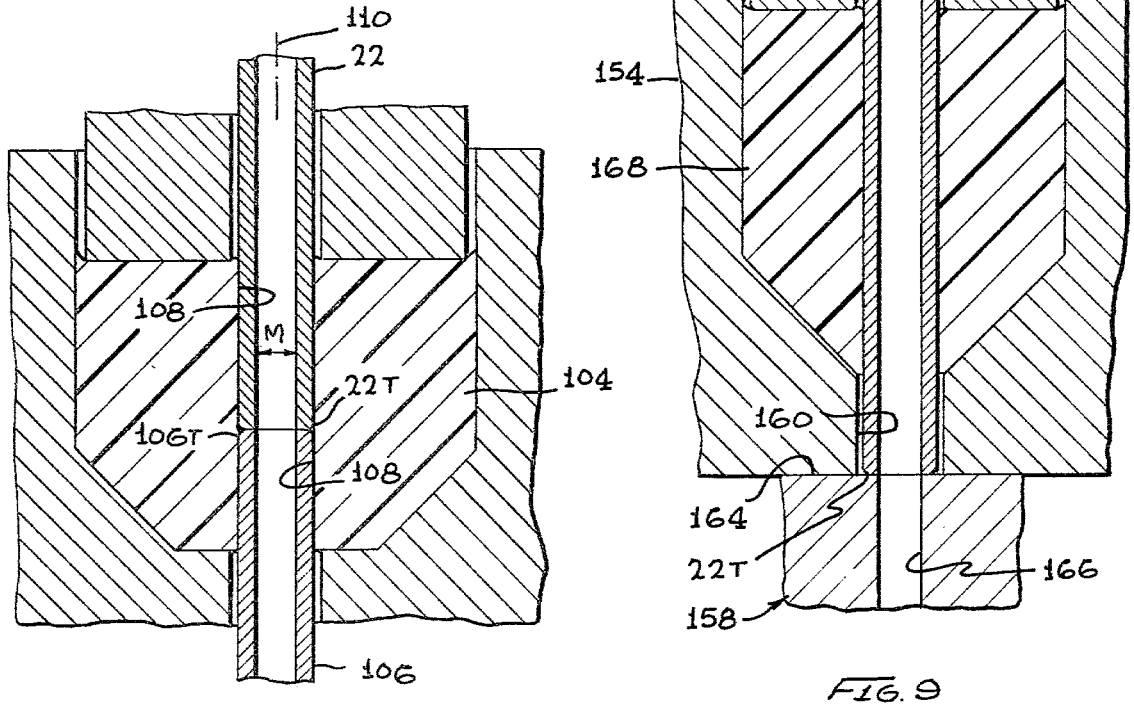
FIG. 6
FIG. 9

SAMPLE INJECTOR

BACKGROUND OF THE INVENTION

Liquid chromatography is a technique in which liquid samples to be analysed are injected into a stream of solvent flowing through a chromatographic column. The sample size to be injected is usually several microliters in volume, but it may vary in size from less than 1 microliter up to 100 microliters or more. The pressure of the solvent stream into which the samples are injected may vary from less than 1000 psi up to 6000 psi or more. It is frequently necessary to analyse large numbers of samples routinely. Automatic sample injection devices are used in these situations. In many cases, the samples are available only in small quantities because they are difficult to isolate.

Automatic sample injection systems are available which make use of a conventional 6-port sample injection valve with a sample loop which must be filled with the sample fluid. Such a device is shown in U.S. Pat. No. 3,918,913 to Stevenson & Coffey. These systems require an appreciable excess of sample to fill the sample loop reliably, and the sample liquid left behind in the connecting tubing between sample vial and valve must be discarded to make way for the next sample. Thus they may use more sample volume than is readily available.

Recent designs of manually operated sample injection devices make use of micro syringes to draw up a sample from a vial and introduce it into an injection valve with little or no loss of sample. Examples are U.S. Pat. Nos. 3,916,692 to Abraham and Hutchins, 3,961,534 to Gundelfinger, and 4,022,065 to Ramin and Stearns. These devices, however, are difficult to automate because the syringe has to be flushed several times between each injection in order to eliminate cross contamination.

There exists a need, therefore, for a sample injection system with the following features: (a) the sample volume can be varied over a range from less than 1 to 100 microliters, (b) there is very little or no sample wastage, and (c) automatic operation can be conducted with high precision and without cross-contamination.

SUMMARY OF THE INVENTION

In accordance with one embodiment of the present invention, a sample injection apparatus is provided which reduces sample wastage essentially to zero and which enables relatively simple automation of sample injection where required. The apparatus includes a long tube or sample loop, and a loop end coupling which can be easily connected and disconnected from an outer end of the sample loop. A valve can be set to connect the inner end of the loop to a micro syringe when the outer end is dipped into a sample container. The syringe plunger is then pulled out to draw the sample into the loop. The outer end of the loop is then connected to the loop end coupling, and the valve can be set to connect the sample loop to the chromatographic column, to flow the sample lying in the loop into the column. By drawing the sample from a vial or other container directly into the outer loop end, from which the sample is then pumped into the column, all of the sample is used. By utilizing this system, there is no loss of sample, the possibility of cross contamination of successive samples is minimized, and sample size can be easily varied from less than 1 microliter up to the capacity of the sample loop.

The alternate connection of the outer loop end to a sample container and to the loop end coupling, can be simplified by utilizing a mechanism that closely guides the loop end in vertical motion. The mechanism lowers the loop end into the coupling and up out of it, and then into a sample container. The sample container can be moved under the raised loop end to enable the loop end to be dipped into the container, and the container can be moved away after the loop end is raised, so that the next downward movement of the loop end brings it into the loop end coupling.

The loop end coupling can include a tube having the same inside diameter as the loop end, and a guiding mechanism for bringing the loop end into alignment with the tube and with their tips into abutment, so that a nonturbulent passageway is provided for the flow of sample from the loop end into the tube of the coupling. A seal mechanism can be operated to seal the loop end against the backward flow of liquid thereabout, and to hold the loop end in place so that the operating pressure of the system will not push the loop end out of the seal.

The novel features of the invention are set forth with particularity in the appended claims. The invention will be best understood from the following description when read in conjunction with the accompanying drawings.

BRIEF DESCRIPTION OF THE DRAWINGS

FIG. 5 is a sectional view of the loop end coupling of the system of FIG. 4.

FIG. 6 is an enlarged view of the region 6—6 of FIG. 5.

FIG. 9 is a partial sectional view of the system of FIG. 8.

DESCRIPTION OF THE PREFERRED EMBODIMENTS

Figure 1:
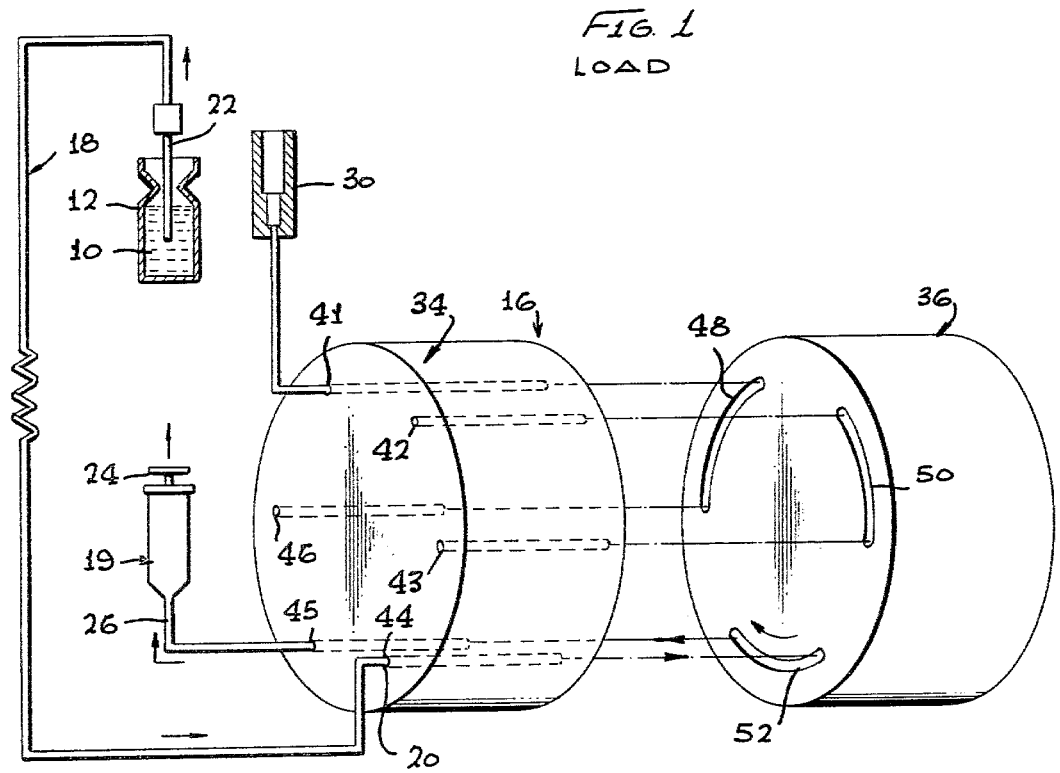
FIG. 1 is a simplified exploded perspective view of a sample injection system constructed in accordance with the present invention, shown in a load configuration wherein a sample liquid is being withdrawn from a container.
Figure 2:
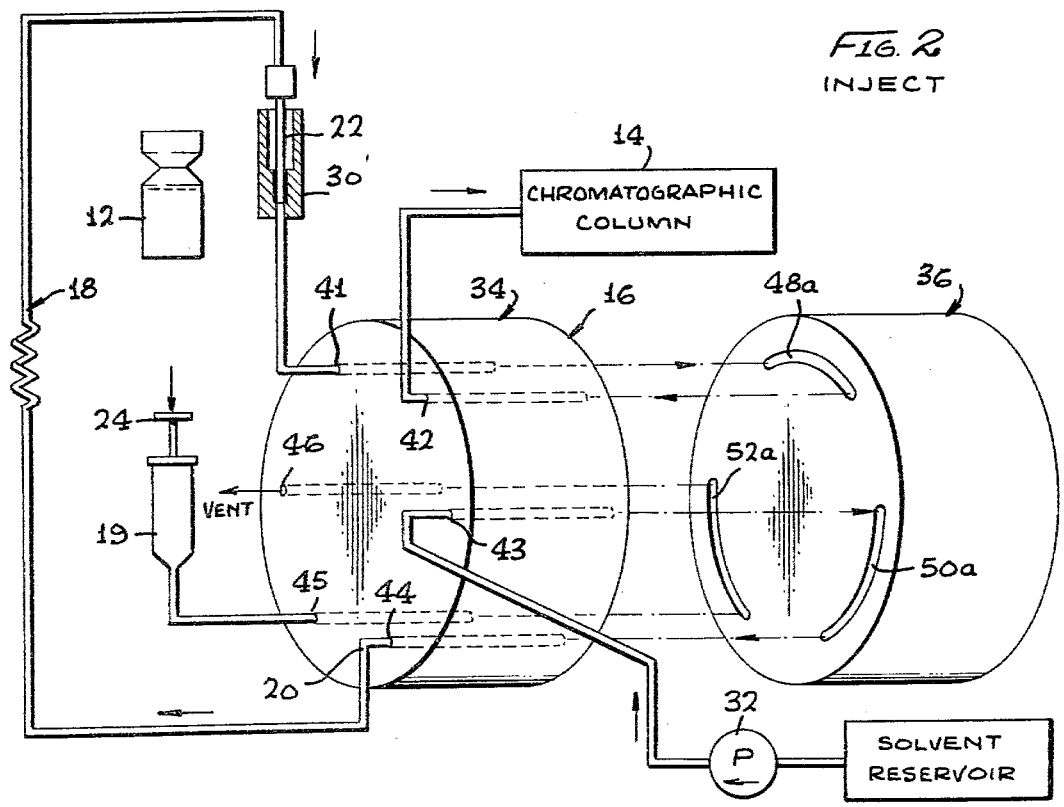
FIG. 2 is a view similar to FIG. 1, but showing the system in an inject configuration wherein the sample is being injected into a chromatographic column.

FIGS. 1 and 2 illustrate two steps in the operation of the present system, whereby sample liquid 10 in a container 12 can be withdrawn from the container and then injected into a chromatographic column 14. As shown in FIG. 1, the system utilizes an injection valve 16 which is connected to a sample loop 18 and a microsyringe 19. The injection valve 16 is a conventional 6-port valve, and the use of a sample loop and microsyringe are known in the art. A novel feature of the system involves the design of the sample loop so that its outer end 22 can be moved as described below. The sample loop 18 is a long narrow tube designed to hold a sample that is to be analyzed, and having an inner end 20 connected to the valve and an outer end 22 which can be moved. In order to "load" the sample loop 18, its outer end 22 is dipped into the container 12, and the syringe 19 is operated by pulling up on the plunger 24 thereof. The injection valve 16 connects a syringe opening 26 to the sample loop inner end 20, so that operation of the syringe causes the sample liquid in the container 12 to be drawn into the loop outer end 22. The syringe, the tubing connecting the syringe to the valve, and the entire sample loop, are initially filled with the pumped solvent so that there is no air in the system which could interfere with the sample analysis.

After the amount of sample liquid, corresponding to the volume displaced by the upward motion of plunger 24, has been drawn into the loop outer end 22, the loop outer end is withdrawn from the container 12 and inserted into a loop end coupling 30, as shown in FIG. 2. In addition, the injection valve 16 is operated to connect different ports thereof to one another. As a result, a pump 32 which pumps a solvent liquid, is connected to the loop inner end 20 to apply pressured liquid thereto. The loop end coupling 30, which is connected to a port of the valve, is connected by the valve to the chromatographic column 14. Therefore, flowing solvent from the pump 32 is pumped into the loop inner end 20, thereby causing the sample in the loop outer end 22 to be pumped into the loop end coupling 30 and to flow through the valve and into the chromatographic column 14. It may be noted that some chromatography can be conducted at low pressures, with a gravity feed device serving as the pumping means that pumps solvent towards the column to pump in the sample, although most work is done under much higher pressures. A high pressure pump means can be formed by a variety of devices, such as a high pressure gas cylinder or a pumping mechanism with moving parts. Following the injection of the sample into the column, the valve 16 can be returned to the load configuration shown in FIG. 1, and the loop outer end 22 can be withdrawn from the loop end coupling and reinserted into the sample container 12 to receive another sample.

Figure 3:
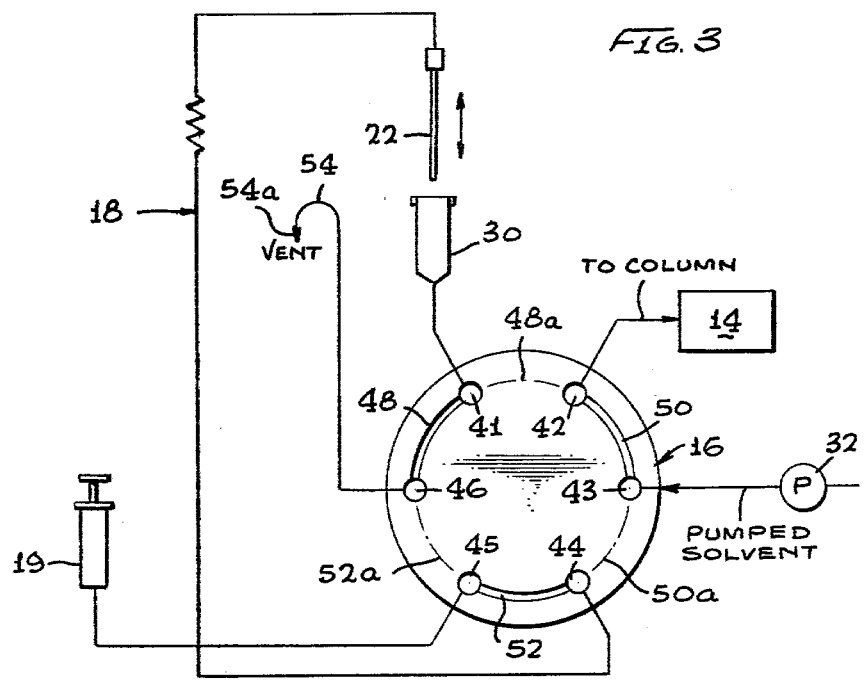
FIG. 3 is a schematic representation of the apparatus of FIG. 1.

The injection valve 16, which is similar to previously known valves, includes a stator element or stator 34 which is connected to various external devices such as the pump, loop, column, and syringe, and a movable element or rotor 36 which can be rotated between the load and inject positions shown in FIGS. 1 and 2. The stator 34 has six ports 41-46 which can be interconnected by passages 48, 50, and 52 formed in the rotor 36. As shown in FIG. 3, wherein the solid lines for passages 48-52 represent the loading position, the valve interconnects the two ports 44, 45 during the loading step, to enable the vacuum applied by the syringe 19 to draw fluid into the loop outer end 22. At this time, solvent pumped by the pump 32 flows into the column 14 to continue the chromatographic analysis. Also, the loop end coupling 30 is connected through the valve to a vent 54.

When the valve 16 is moved to its inject configuration, the interconnection of the ports are as indicated by the positions of the passages at 48a, 50a, and 52a. In this configuration, solvent is carried through passage 50a to the loop 18, so that the sample in the loop end 22 can be pumped into the loop end coupling 30 (the outer loop end will have already been connected to the coupling 30). The sample then can flow through the passage at 48a to the column 14. At the same time the plunger of microsyringe 19 can be moved downwardly towards its initial position, which causes the syringe to pump out solvent lying therein. The syringe is coupled through the valve passageway 52a to a vent 54, to discharge the solvent as into a sink leading to a sewer. It may be noted that vent 54 includes a tube with an end 54a lying at a higher level than the middle of the loop end coupling 30. This assures that when the valve is returned to the load configuration, excess solvent lying in the coupling 30 will not be drained therefrom through the vent 54 by siphon action. Draining away of solvent should be avoided in as much as any air in the path between the loop end coupling 30 and valve, otherwise could be pumped into the column.

Figure 4:
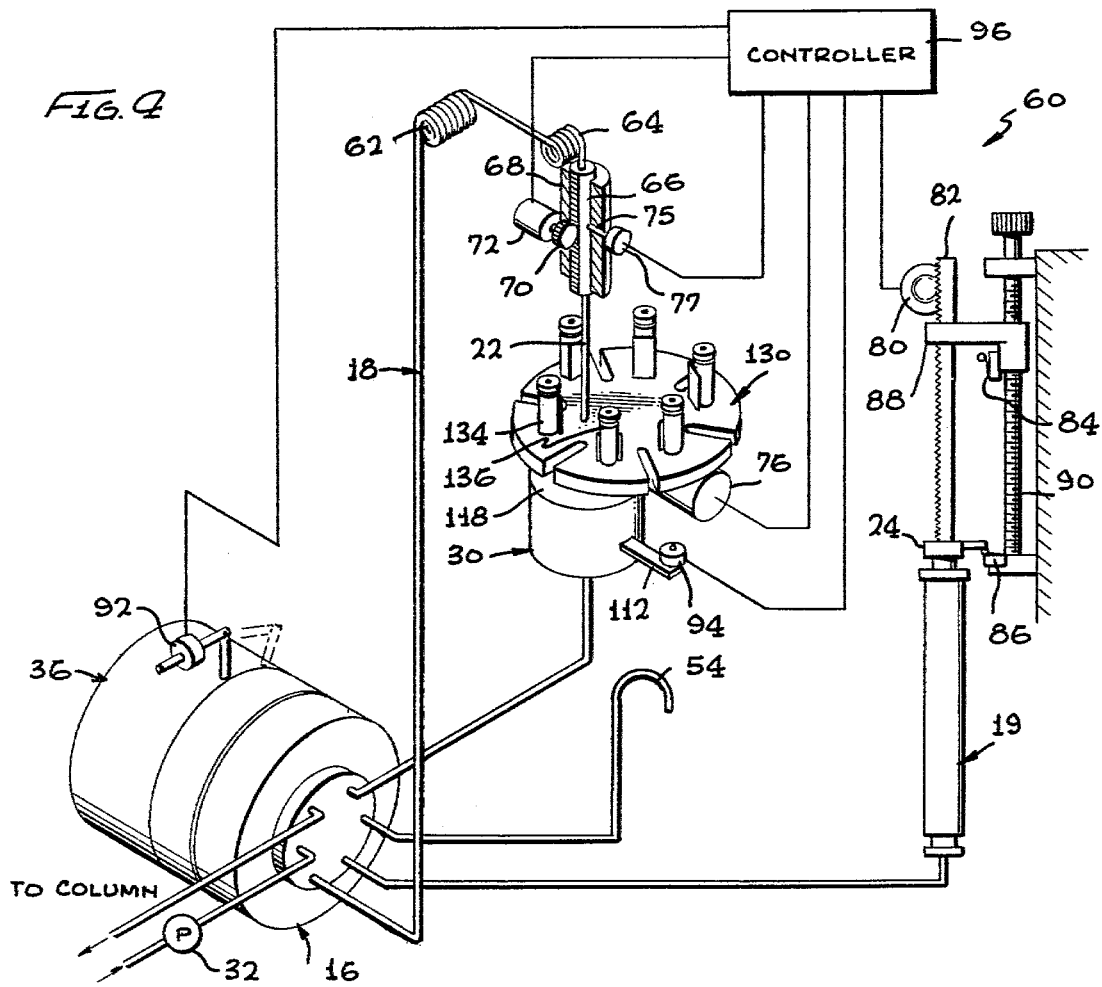
FIG. 4 is a perspective view of an automatic sample injection system.

FIG. 4 illustrates details of a sample injection system 60 which is an automatic version of the system of FIGS. 1-3. The sample loop 18 comprises a long narrow tube having a pair of coils at 62 and 64 that facilitate movement of the loop outer end. The loop outer end is held by an inner guide 66 which is closely confined to vertical motion by an outer guide 68. A gear 70 powered by a motor 72, is engaged with a rack on the inner guide 66 to produce controlled up and down movement of the loop outer end 22. Vials 134, 136 containing sample to be analyzed, are mounted on a carriage device in the form of a turntable 130 that is indexed by a motor 76, to move each vial between a position directly under the loop end 22 and a position laterally spaced therefrom. In the operation of the system, the loop end motor 72 is operated to lift the loop end 22 above the level of the vials, the motor 76 is operated to move a next vial under the loop end, and the loop end motor 72 is again operated to lower the loop end into the vial. After the loop end has been filled with the required amount of sample, it is lifted, the vial is moved to one side, and the loop end 22 is lowered into the loop end coupling 30. A lock 75 operated by a solenoid 77, locks the loop end guide 66 in its downward position, to hold the loop end in the coupling 30 during transfer of the sample into the column, to avoid upward movement of the loop end where the sample is pumped under high pressure.

The syringe 19 which is utilized to apply a vacuum that draws sample liquid into the loop, is operated by a motor 80 that drives a rack 82 connected to the plunger 24 of the microsyringe. The syringe motor 80 can be operated to lift the plunger 24 out of the cylinder of the microsyringe, until a switch 84 senses the plunger is in its upward position. The syringe motor can lower the plunger 24 until another switch 86 senses that the plunger is in its downward position.

The amount of sample liquid that is to be drawn into the loop should be accurately controlled, and the amount may vary for different procedures. By closely controlling the stroke of the microsyringe, the system accurately controls the amount of sample drawn into the loop. The stroke of the microsyringe can be varied by turning a screw 90 on which the bracket 88 is mounted, to lift or lower the sensor switch 84. It may be noted that the microsyringe not only serves as a device that can apply a vacuum to the sample loop to draw in liquid therein, but also serves as a device that closely controls the amount of liquid to be drawn in. If the sample is available in a container that can be pressured, then the microsyringe does not have to apply a vacuum to draw in the liquid, but it still serves as a means to closely control the amount of liquid drawn into the loop.

The system 60 is also controlled by the use of a valve actuator 92 that turns the rotor 36 of the valve 16 between its load and inject positions. Also, a solenoid 94 is provided at the loop end coupling 30 to seal the outer loop end 22 during the injection phase of system operation, as will be described below. The operation of the various motors and solenoids all can be controlled by a controller 96 which may include a microprocessor or a cam shaft having multiple cams for operating switches.

FIGS. 5 and 6 illustrate details of the loop end coupling 30 which is designed to rapidly connect and disconnect from the loop outer end 22. The coupling includes a guide plunder 100 with a guideway 102 which can receive the loop end 22, and a loop end seal 104 which can receive the tip portion of the loop end 22. The seal 104 also receives the tip portion of a coupling tube 106, to form a liquid-tight seal around the adjacent tips of the loop end 22 and coupling tube 106.

The loop end seal 104 is constructed of an inert and easily compressible material such as Teflon, and has a through hole 108 which is large enough to readily receive the loop end 22. After the tip portion of the loop end is received in the seal 104, the seal is axially compressed, along the axis 110 of the tubes, to cause the seal to contract about the loop end 22 to hold the loop end in place and form a fluid-tight seal thereagainst. The guide 100 can be slid a small distance along the axis 110 to cause such compression, and a lever 112 is provided to press the guide against the loop seal 104. The lever 112 has a first end 114 that can bear against a fulcrum 116 mounted on a frame 118 of the loop end coupling, has a middle portion 120 that bears against the flange on the guide 100, and has an opposite end 122 which can be moved down to force down the guide 100 and thereby compress the seal 104 sufficiently to hold the loop end 22 and to form a liquid-tight seal. The solenoid 94 can be utilized to automatically compress the lever after the loop end 22 has been inserted into the seal.

Tight contraction of the seal 104 (FIG. 5) around the loop end 22, is especially important where the sample is pumped at high pressure into the column, since the high pressure tends to cause leakage and tends to push the loop end up out of the coupling. The lock 75 (FIG. 4) which holds down the loop end guide 66, prevents excessive upward movement of the loop end, while the seal 104 is useful to further prevent even a slight upward movement of the tip of the loop end.

It may be noted that the frame 118 includes a drain passage 124, which is utilized to carry away excess solvent that fills and overflows the guide 100. Such solvent is received from the vent port 46 of FIG. 3 during the load phase of system operation.

It is desirable to obtain a smooth laminar flow of the sample from the outer tube end 22 to the coupling tube 106 of the loop coupling. FIG. 6 illustrates details of the sample loop end 22 and of the coupling tube 106, through which the sample passes. In order to facilitate the flow between the tubes, they are constructed with inside diameters M which are substantially the same, and are held with their open tips 22T and 106T abutting one another during the injection phase of operation. Both tips are formed flat immediately around their inside passages, to enable close abutment of the tips, so that there is little if any space between the abutting tips. The hole 108 in the seal is of substantially constant diameter, and the loop end 22 and coupling tube 106 have the same outside diameter. In one sample injector system that has been designed, the loop end 22 was a hardened stainless steel needle having an outside diameter of 28 mil (thousandths of an inch) and an inside diameter M of 16 mil. The coupling tube 106 was formed with the same inside and outside diameters, although the diameters could be different if desired.

FIG. 5 shows a portion of the turntable 130, which has vial holders 132 that can hold a number of different vials 134, 136. The turntable 130 is formed with apertures 138 between the vial positions, to enable the loop outer end 22 to pass down into the loop coupling 30 during the injection phase of operation. After each injection, the loop end 22 is raised above the vial, the turntable 130 is indexed to bring a next vial under the raised loop end 22, and the loop end 22 is then partially lowered into the vial to permit the next load phase of operation to occur. The same system can be utilized for either the repeated withdrawal of samples from a single bottle or different samples from a succession of vials, and in fact a turntable can be utilized for withdrawing samples from a single container by operating the turntable to rotate back and forth instead of repeatedly indexing by small angles in a single direction.

The apparatus shown in FIG. 4 for guiding the loop end 22 in vertical motion, is separate from the apparatus for applying a vacuum or otherwise drawing a sample into the loop end, and is also separate from the apparatus for alternately dipping the loop end into the loop end coupling and into containers of sample liquid. This simplifies the construction of the system. It should be noted that the system can be manually operated instead of automatically controlled by a controller. Such manual operation can be conducted either by providing switches that can be manually operated to activate each of the motors and solenoids, or by providing handles on the elements to be moved, to enable manual movement thereof. Manual operation can be desirable where one or a few samples are to be injected, and a technician wishes to time the operation himself rather than program the controller to time it.

Even for manual operation, the system 60 has considerable advantages over a prior art system which involves the dipping of a syringe into a sample vial and the transfer by way of the syringe and injection valve into the sample loop. Where a syringe is utilized to withdraw the sample and inject it into the valve, some of the sample will normally remain in the syringe, and the syringe will have to be flushed several times to avoid cross contamination of the next sample, requiring more time to perform the procedure. It may be noted that there is a possibility of cross contamination of sample in the apparatus of FIG. 5, due to the possibility of the sample in one vial clinging to the outside of the loop end 22. However, such contamination is small since there is some flushing of the outisde of the loop end 22 when it next dips into the guide 100 which is refilled with solvent after every operation. Where cross contamination is considered a problem, provisions can be made for additional flow of solvent into the loop end coupling via the vent tube 54. The overflow opening 124 will accommodate this additional flushing liquid.

Figure 7:
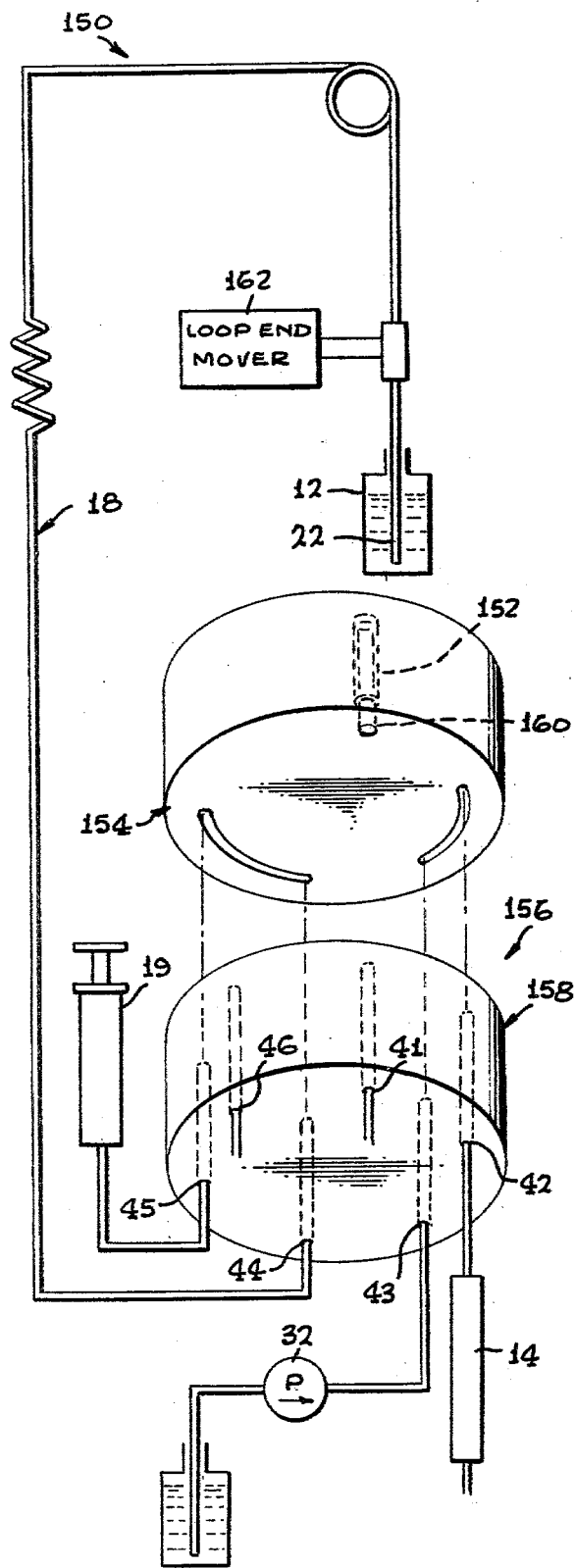
FIG. 7 is a simplified exploded perspective view of a sample injection system constructed in accordance with another embodiment of the invention, shown in a load configuration.
Figure 8:
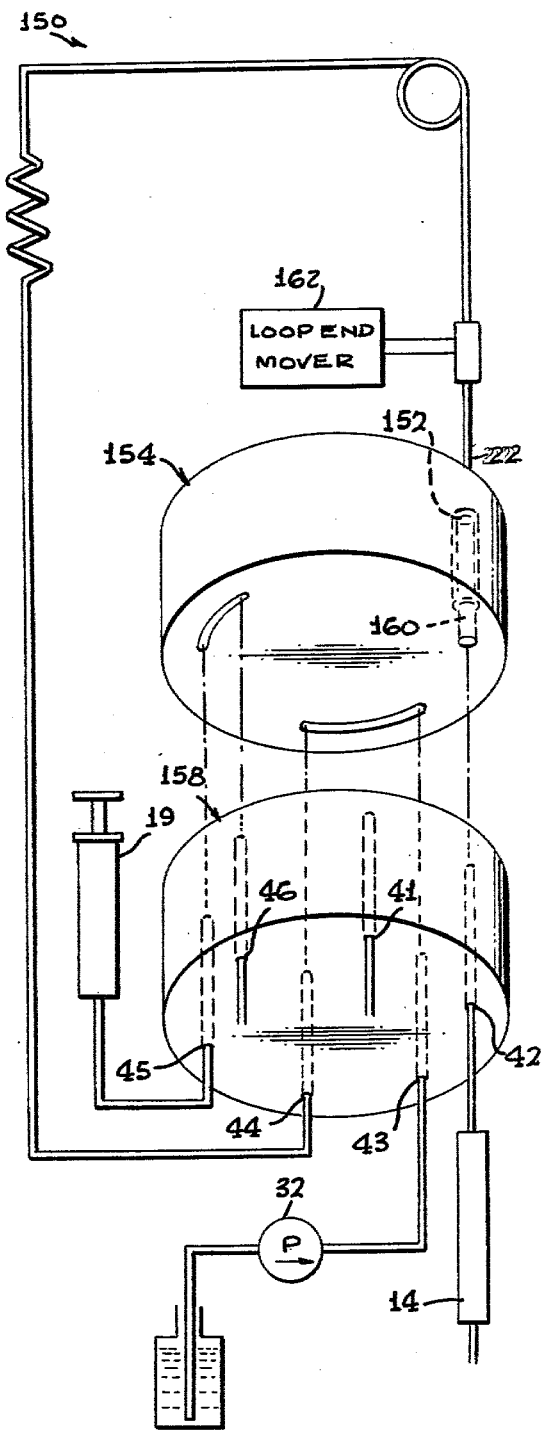
FIG. 8 is a view similar to that of FIG. 7, but with the system in an inject configuration.

FIGS. 7-9 illustrate another sample injector system 150 which minimizes the length and convolution of the flow path, between the outer end 22 of the loop and a chromatographic column 14 during injection of a sample into the column. This is accomplished by forming a loop end coupling 152 in one of the elements 154 of an injection valve 156 that includes a stator element 158 and a rotor element 154. The stationary element 158 is similar to the element 34 of FIG. 1. However, the rotor element 154 is designed with a through passage 160 therein, with the upper end forming part of the loop end coupling 152. FIG. 7 illustrates the load configuration of the system, wherein a loop end moving mechanism 162 moves the loop end 22 into a container 12 that contains the sample liquid. FIG. 8 shows the system in an inject configuration wherein the outer loop end 22 has been inserted into the loop end coupling 152 and clamped in place, and the rotor 154 has been moved to a position wherein the loop end coupling 152 and through hole 160 are aligned with a port 42 in the stator that leads to the chromatographic column 14.

FIG. 9 shows some of the details of the loop end coupling 152 which receives the loop end 22. The through hole 160 which forms part of the loop end coupling can receive the needle-like loop end 22 so that the tip 22T of the loop end can lie flush with a surface 164 of the stator element 158 at the interface of the valve elements 154, 158 where their surfaces are adjacent and in contact. A hole 166 in the stator element, which forms a tube, has approximately the same inside diameter as the loop end 22. The alignment of the loop end tip 22T with the hole 166 that forms part of the port of the stator, and their closeness in inside diameter, results in a substantially laminar flow of the sample from the loop end 22 into the hole 166, and from there to the chromatographic column. The laminar flow minimizes mixing of the sample with the solvent liquid that will previously have filled the hole 166, so that higher resolution analysis of the sample can be achieved by the column. The loop end coupling 152 includes a seal 168 that closely surrounds the loop end 22, and a plunger 170 which can be pressed down to compress the seal 168 so that it becomes squeezed tightly about the loop end. The chromatographic column can be connected very close to the valve port 42 which is at the end of hole 166, so that the sample flows into the column with minimal delay and with minimal dilution. It may be noted that a loop end coupling can be connected directly to the column, but the solvent flow to the column would then have to be stopped during the sample loading process. The use of an intervening valve permits the solvent flow to continue while loading the next sample.

Thus, the invention provides a sample injecting system for withdrawing a sample liquid from a vial or other container and injecting it into a chromatographic column or other analyzing device, which minimizes the possibility of sample loss and cross contamination, and which can give improved resolution. This is accomplished by the use of a sample loop with an outer end that can be readily connected and disconnected from a loop end coupling. The loop end therefore can be dipped into the container to draw in the sample, and then connected to the coupling to discharge the sample for flow to the column. A mechanism can be provided to move the loop end vertically, to alternately dip it into a container holding the sample liquid, raise it therefrom, and then lower the loop end into the coupling. The reception of the sample directly into the loop end, from which it is later discharged under high pressure, minimizes the passages through which the sample is transferred, to thereby minimize sample loss, cross contamination, and sample dilution.

Although particular embodiments of the invention have been described and illustrated herein, it is recognized that modifications and variations may readily occur to those skilled in the art and consequently, it is intended that the claims be interpreted to cover such modifications and equivalents.

The embodiments of the invention in which an exclusive property or privilege is claimed are defined as follows:

1. In a sample injecting system which includes a sample loop with inner and outer ends, for receiving a sample liquid originally held in a container, and means for pumping a liquid into the loop to inject a sample therefrom into a chromatographic column or other analyzing device, the improvement comprising:

a loop end coupling for detachably receiving said loop outer end;

means for connecting said loop end coupling to said analyzing device;

motor means for moving said loop outer end downwardly into a container and upwardly out of the container, and downwardly into said loop end coupling and upwardly out of the coupling;

means for withdrawing a liquid; and means for alternately connecting said inner loop end to said means for withdrawing a liquid and to said pumping means.

2. A sample injecting apparatus for withdrawing sample liquid held in a container and injecting it into a chromatographic column or other analyzing device, comprising:

a sample loop which includes a tube, said loop having inner and outer ends;

a loop end coupling;

withdrawing means for drawing a liquid into the loop;

pump means for pumping a liquid; and a valve coupled to said loop inner end, said withdrawing means, said pump means, said loop coupling, and said analyzing device, said valve movable between a load configuration wherein it couples said withdrawing means to said loop inner end to draw liquid into said loop, and an inject configuration wherein it couples said pump to said loop inner end and couples said loop end coupling to said analyzing device to carry liquid into said analyzing device;

said loop outer end being connectable alternately to said container and said loop end coupling, said withdrawing means being operable to draw in liquid when said loop outer end is connected to said container and said valve is in said load configuration, to fill the loop outer end with said liquid, and said valve being movable to said inject configuration when said outer loop end is connected to said loop end coupling, to pump the liquid into the analyzing device;

said sample loop outer end includes a hollow needle with an open tip; and said loop end coupling includes means forming a conduit with an end that has approximately the same inside diameter as said needle tip, and also includes means for sealingly holding said needle tip and conduit end in alignment and in abutment with one another.

3. A method for injecting samples of liquid held in a container, into a chromatographic column or other analysing device, comprising:

alternately moving a first end of a sample loop into the container and then out of the container and into connection with a loop end coupling which is connected to the analyzing device; and alternately connecting a second end of the loop to the inlet of a vaccum pumping device when the first loop end is in the container, and then connecting the second loop end to the outlet of a pump means when the first loop end is connected to the analyzing device; and wherein said first loop end includes a tube with an open tip and said loop end coupling includes a coupling tube with an open tip; and said step of moving said first loop end into connection with a loop end coupling, includes moving said tubes into alignment and with their tips in abutment, and sealing the region around said tube tips against the leakage of liquid therefrom.

4. In a sample injecting system which includes a sample loop with inner and outer ends, for transferring a sample liquid originally held in a container into the loop and then injecting the sample therefrom into a chromatographic column or other analyzing device, the improvement comprising:

a loop end coupling for detachably receiving said loop outer end;

means for connecting said loop end coupling to said analyzing device;

means for moving said loop outer end alternately into a container and into said loop end coupling;

means for transferring a sample liquid into said loop outer end when it lies in said container; and means for flowing a liquid into said inner loop end when the outer loop end has been moved into said loop end coupling, to flow sample liquid from the outer loop end through the coupling to the analyzing device;

said outer loop end having an opening at its extreme tip, said loop end coupling comprising walls forming a substantially straight hole with one end constructed to closely receive said outer loop end and an opposite second end, and said coupling including a tube connecting said second end of said hole to said analyzing device, said hole being devoid of any opening between said ends thereof, and said means for moving said loop outer end is constructed to alternately withdraw said loop outer end completely from said hole and to later insert it partially through said hole.

5. The system described in claim 4 wherein:

said coupling includes a seal member forming said straight hole, said hole being of approximately the same diameter as said loop outer end to receive said loop outer end, and said tube which is connected to said an end lying in said hole and positioned to abut the end of said loop outer end.

6. In a sample injecting apparatus for withdrawing sample liquid from a container into a tube outer end which has the form of a needle with an open tip, and then connecting the tube outer end to a chromatographic column or other analyzing device to inject the sample thereto, the improvement of a coupling for receiving the tube outer end and connecting it to the analyzing device, comprising:

a seal member having a hole with at least one end of a diameter approximately equal to the outer diameter of said tube outer end;

means forming a conduit for carrying fluid from said hole to said analyzing device, said conduit forming a shoulder lying in said hole in said seal member to directly abut the tube outer end; and a guide having a guideway aligned with said hole in said seal member, to guide a tube outer end into said seal member to abut said shoulder.

7. The improvement described in claim 6 wherein:

said seal member hole extends substantially straight through said seal member, and said conduit includes a coupling tube with one end lying in said hole and having a tip positioned to directly abut said tube outer end.

8. The improvement described in claim 7 including:

motor means for completely withdrawing said tube outer end from said seal member, dipping said tube outer end into a sample-holding container to enable the reception of a sample in the tube outer end, and again inserting said tube outer end into said seal member until the tip of the seal member abuts the shoulder therein whereby to enable the pumping out of sample in the tube outer end and through the conduit to the analyzing device.

* * * * *